United States Patent [19]

Pham et al.

[11] Patent Number: 5,624,449
[45] Date of Patent: Apr. 29, 1997

[54] ELECTROLYTICALLY SEVERABLE JOINT FOR ENDOVASCULAR EMBOLIC DEVICES

[75] Inventors: Pete P. Pham, Fremont; Hong Doan, Santa Clara; Ivan Sepetka; Joseph Eder, both of Los Altos; Edward Snyder, San Jose, all of Calif.

[73] Assignee: Target Therapeutics, Fremont, Calif.

[21] Appl. No.: 431,827

[22] Filed: Apr. 28, 1995

Related U.S. Application Data

[63] Continuation-in-part of Ser. No. 147,529, Nov. 3, 1993, Pat. No. 5,423,829.
[51] Int. Cl.⁶ .................................................. A61B 17/00
[52] U.S. Cl. ......................... 606/108; 606/1; 606/32; 606/41; 128/772
[58] Field of Search ............................ 606/1, 32–34, 606/108, 41, 45, 47, 191; 128/772; 604/57

[56] References Cited

U.S. PATENT DOCUMENTS

| | | |
|---|---|---|
| 3,868,956 | 3/1975 | Alfidi et al. . |
| 4,512,338 | 4/1985 | Balko et al. . |
| 4,739,768 | 4/1988 | Engelson . |
| 4,884,579 | 12/1989 | Engelson . |
| 4,994,069 | 2/1991 | Ritchart et al. . |
| 5,108,407 | 4/1992 | Geremia et al. . |
| 5,122,136 | 6/1992 | Guglielmi et al. . |
| 5,250,071 | 10/1993 | Palmermo . |
| 5,354,295 | 10/1994 | Guglielmi et al. . |
| 5,380,320 | 1/1995 | Morris et al. . |

FOREIGN PATENT DOCUMENTS

WO94/10936  5/1994  WIPO .

*Primary Examiner*—Angela D. Sykes
*Assistant Examiner*—Michael Peffley

[57] ABSTRACT

This invention is an apparatus for endovascular occlusion through the formation of thrombi in arteries, veins, aneurysms, vascular malformations, and arteriovenous fistulas. In particular, it deals with an improved sacrificial link between an endovascular device which is introduced to and is intended to remain at the desired thrombus formation site and the device used to introduce the device. The invention further includes a method for introduction of the device and its electrolytic separation.

10 Claims, 4 Drawing Sheets

ELECTROLYTICALLY SEVERABLE JOINT FOR ENDOVASCULAR EMBOLIC DEVICES

RELATED APPLICATIONS

This is a continuation-in-part of U.S. patent application No. 08/147,529, filed Nov. 3, 1993, entitled "ELECTROLYTICALLY SEVERABLE JOINT FOR ENDOVASCULAR EMBOLIC DEVICES" (now U.S. Pat. No. 5,423,829), the entirety of which is incorporated by notice.

FIELD OF THE INVENTION

This invention is an apparatus for endovascular occlusion through the formation of thrombi in arteries, veins, aneurysms, vascular malformations, and arteriovenous fistulas. In particular, it deals with an improved sacrificial link between an endovascular device which is introduced to and is intended to remain at the desired thrombus formation site and the device used to introduce the device. The invention further includes a method for introduction of the device and its electrolytic separation.

BACKGROUND OF THE INVENTION

Approximately 25,000 intracranial aneurysms rupture each year in North America. The primary purpose of treatment for a ruptured intracranial aneurysm is to prevent rebleeding. There are a variety of ways to treat ruptured and non-ruptured aneurysms.

Possibly the most widely known of these procedures is an extravascular approach using surgery or microsurgery. This treatment is common with intracranial berry aneurysms. The method comprises a step of clipping the neck of the aneurysm, performing a suture ligation of the neck, or wrapping the entire aneurysm. Each of these procedures is formed by intrusive invasion into the body and performed from the outside of the aneurysm or target site. General anesthesia, craniotomy, brain retraction, and placement of a clip around the neck of the aneurysm are typically required in these surgical procedures. The surgical procedure is often delayed while waiting for the patient to stabilize medically. For this reason, many patients die from the underlying disease or defect prior to the initiation of the procedure.

Another procedure—the extra-intravascular approach—involves surgically exposing or stereotactically reaching an aneurysm with a probe. The wall of the aneurysm is then perforated from the outside and various techniques are used to occlude the interior in order to prevent it from rebleeding. The techniques used to occlude the aneurysm include electrothrombosis, adhesive embolization, hog hair embolization, and ferromagnetic thrombosis. These procedures are discussed in U.S. Pat. No. 5,122,136 to Guglielmi et al., the entirety of which is incorporated by notice.

A still further approach is the least invasive and is additionally described in Guglielmi et al. It is the endovascular approach. In this approach, the interior of the aneurysm is entered by use of a catheter such as those shown in Engelson (Catheter Guidewire) U.S. Pat. No. 4,884,579 and also in Engelson (Catheter for Guidewire Tracking), U.S. Pat. No. 4,739,768. These patents describe devices utilizing guidewires and catheters which allow access to the aneurysm from remote portions of the body. Specifically by the use of catheters having very flexible distal regions and guidewires which are steerable to the region of the aneurysm, embolic devices which may be delivered through the catheter are an alternative to the extravascular and extra-intravascular approaches.

The endovascular approach typically includes two major sections. The first section involves the introduction of the catheter to the aneurysm site using devices such as shown in the Engelson patents. The second section often involves filling the aneurysm in some fashion or another. For instance, a balloon may be introduced into the aneurysm from the distal portion of the catheter where it is inflated, detached, and left to occlude the aneurysm. In this way, the parent artery is preserved. Balloons are becoming less in favor because of the difficulty in introducing the balloon into the aneurysm sac, the possibility of an aneurysm rupture due to overinflation of the balloon within the aneurysm, and the risk associated with the traction produced when detaching the balloon.

A highly desirable embolism-forming device which may be introduced into an aneurysm using endovascular placement procedures, is found in U.S. Pat. No. 4,994,069, to Ritchart et al. There is described a device—typically a platinum/tungsten alloy coil having a very small diameter—which may be introduced into an aneurysm through a catheter such as those described in Engelson above. These coils are often made of wire having a diameter of 2-6 mils. The coil diameter may be 10-30 mils. These soft, flexible coils may be of any length desirable and appropriate for the site to be occluded. For instance, the coils may be used to fill a berry aneurysm. Within a short period of time after the filling of the aneurysm with the embolic device, a thrombus forms in the aneurysm and is shortly thereafter complemented with a collagenous material which significantly lessens the potential for aneurysm rupture.

Coils such as seen in Ritchart et al. may be delivered to the vasculature site in a variety of ways including, e.g., mechanically detaching them from the delivery device as is shown in U.S. Pat. No. 5,250,071, to Palermo or by electrolytic detachment as is shown in Guglielmi et al. (U.S. Pat. No. 5,122,136) as was discussed above.

Guglielmi et al. shows an embolism-forming device and procedure for using that device. Specifically, Guglielmi et al. fills a vascular cavity such as an aneurysm with an embolic device such as a platinum coil which coil has been endovascularly delivered. The coil is then severed from its insertion tool by the application of a small electric current. Desirably, the insertion device involves a guidewire which is attached at its distal end to an embolic device by an electrolytic, sacrificial joint. Guglielmi et al. suggests that when the embolic device is a platinum coil, the platinum coil may be 1-50 cm. or longer as is necessary. Proximal of the embolic coil is a guidewire, often stainless steel in construction. The guidewire is used to push the platinum embolic coil, obviously with great gentleness, into the vascular site to be occluded. The patent shows a variety ways of linking the embolic coil to the pusher guidewire. For instance, the guidewire is tapered at its distal end and the distal tip of the guidewire is soldered into the proximal end of the embolic coil. Additionally, a stainless steel coil is wrapped coaxially about the distal tapered portion of the guidewire to provide column strength to the guidewire. This coaxial stainless steel wire is joined both to the guidewire and to the embolic coil. Insulation may be used to cover a portion of the strength-providing stainless steel coil. This arrangement provides for two regions which must be electrolytically severed before the embolic coil is severed from the guidewire.

A further variation of the Guglielmi detachable coil is one in which the distal tip of the stainless steel guidewire is not soldered to the proximal end of the embolic device. A simple conical stainless steel wire is included from the stainless steel guidewire to the embolic coil.

A further variation found in Guglielmi et al. includes a thin, threadlike extension between the guidewire core and the proximal end of the embolic coil. In this way, the guidewire does not extend to the embolic coil, but instead relies upon a separately introduced extension.

A continuation-in-part application to the Guglielmi et al patent discussed above, U.S. Pat. No. 5,354,295, "IMPROVEMENTS IN AN ENDOVASCULAR ELECTROLYTICALLY DETACHABLE WIRE AND TIP FOR THE FORMATION OF THROMBUS IN ARTERIES, VEINS, ANEURYSMS, VASCULAR MALFORMATIONS AND ARTERIOVENOUS FISTULAS" issued Oct. 11, 1994, describes the use of mechanically detachable embolic devices as well as those which are electrolytically detachable. The embolic devices may be augmented with attached filaments.

Dr. Taki has devised a variation of the Guglielmi detachable coil using a copper link between the guidewire and the coil.

None of the noted procedures using electrolytically detachable embolic devices suggests the structure of the sacrificial link described herein.

SUMMARY OF THE INVENTION

As noted above, this invention is a device for forming a vascular occlusion at a selected site. Generally, the device comprises a guidewire having a distal tip which distal tip may be introduced into the selected vascular site or cavity. The guidewire is joined to the distal tip or embolic device in such a way that the vascular device may be electrolytically detached by application of a current to the core or guidewire. The improvement involves the use of a discrete, sacrificial link between the core wire and the vascular device to allow clean and quick detachment from the guidewire. Specifically the most desirable of the improved sacrificial joints is a narrow band which has been cut from a coating, e.g., a polymeric coating adherent to the metallic substrate, perhaps by laser cutting. The focussed electrolysis found at the sacrificial site reduces the overall possibility of occurrence of multiple electrolysis sites and liberation of large particles from those sites.

There are several variations of the sacrificial joint involving extensive electrical insulation about the core wire and any supporting coil devices or the use of direct coating on electrolytically susceptible surfaces. The most desirable of the improved sacrificial joints is a narrow band which has been cut from a coating, e.g., a polymeric coating adherent to the metallic substrate, perhaps by laser cutting.

DESCRIPTION OF THE INVENTION

Each of the discrete sacrificial joints discussed below may be used in the device shown in U.S. Pat. No. 5,122,136 to Guglielmi et al., the entirety of which patent is incorporated by reference.

Figure 1:
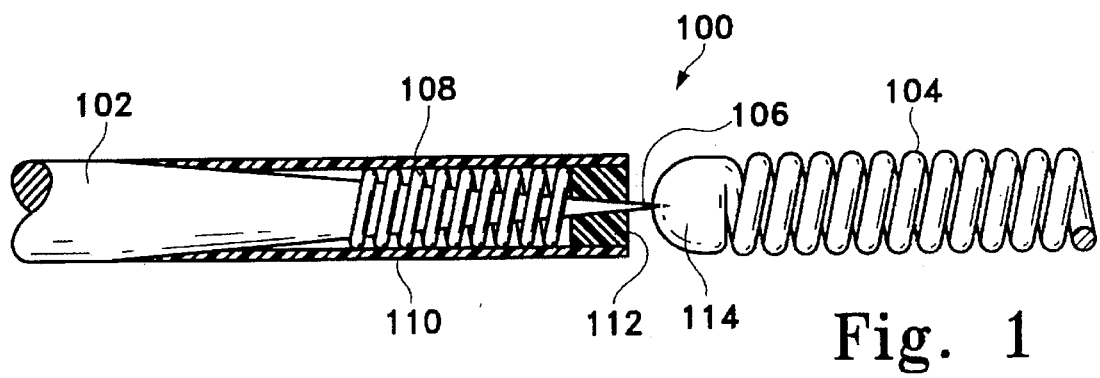
FIGS. 1, 2, 3, 5, and 6 show sideview, partial cross-sectional views of variations of the inventive, electrolytically susceptible, sacrificial link between a core wire and an embolic device.

The first of such variations is shown in FIG. 1. The assembly 100 is made up generally of a guide or core wire 102 which tapers at its distal end to a point and is soldered into the proximal end of a vasoocclusive device 104, which in this case is a coil. All of the core wire 102 is covered with an insulating material such as polyfluorocarbons (e.g., Teflon®), polyurethane, polyethylene, polypropylene, polyimides, or other suitable polymeric material, except the most distal exposed joint or sacrificial link 106. Link 106 is not coated with an electrical insulator and is of a material which is susceptible to electrolytic dissolution in blood. The core wire 102 is typically stainless steel and may be disposed within a protective catheter not shown. Stainless steel guidewire 102 typically is approximately 10–30 mils. in diameter. Often the guidewire is 50–300 cm. in length, that is to say, from the entry site outside the body to sacrificial link 106.

Sacrificial link 106 is a discrete link. By "discrete" we mean to say preferably that the joint is substantially dissolved upon release of the vasoocclusive device 104. Alternatively, "discrete" may be meant to mean that the length of the link 106 is no greater than the diameter of the sacrificial link 106 or that the electrolytic surface present after the vasoocclusive device is released is not substantially greater than would be a circle having the diameter of the sacrificial link 106.

Also shown in FIG. 1 is a coil 108 which is soldered at its proximal end and, typically, is designed to provide some column strength to the guidewire assembly while not detrimentally affecting the flexibility of the tapered portion of the core wire 102. Obviously, in the area where the support coil 108 is soldered to core wire 102, the coating on 102 is not present so to allow the solder to adhere to metal surfaces. Further, on the distal tip of core wire 102 may be found a pair of insulators: sleeve 110 and end plug 112 which serve to further remove the stainless steel coil 108 from contact with the blood while the step of electrolytic detachment is carried out. Preferably, the end plug 112 and sleeve 110 are adhesively attached to each other so to form an electrically insulating or electrolysis-tight housing about coil 108. The end plug 112 and sleeve 110 form a planar surface in the Figure which is generally planar and perpendicular to the axis of the core wire 102.

As noted above, the distal end of guidewire or core wire 102 is inserted into the solder joint 114 forming the proximal end of vasoocclusive device 104.

As will be discussed in more detail below, the discrete sacrificial link 106 is completely or substantially completely dissolved during electrolysis.

Figure 2:
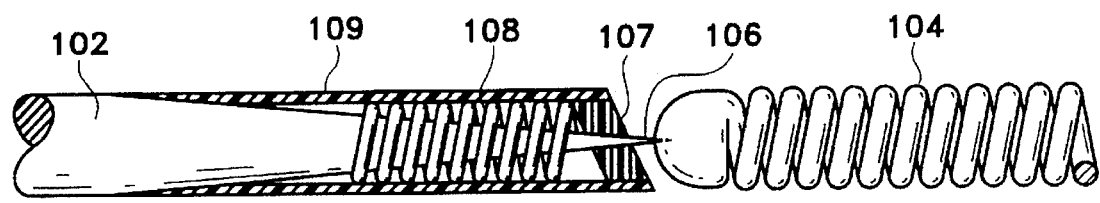

FIG. 2 shows a most preferred variation of the FIG. 1 device having a guide or core wire 102 which may taper at its distal end to a point and which is soldered into the proximal end of a vasoocclusive device 104, which in this case is a coil. Similarly, the distal portion of the guidewire 102 having stainless steel coil 108 thereabout is all enclosed in an end plug 107 and sleeve 109 to provide additional protection to the guidewire and included stainless steel coil 108. The major difference between the FIG. 1 device and the link assembly shown in FIG. 2 is the use of a bias formed distal region. The combination of end plug 107 and sleeve 109 allow clear access by blood (and therefore electrolytic current) to the sacrificial link (106). The end plug 112 and sleeve 110 form a planar surface in the Figure which is generally planar but not perpendicular to the axis of the core wire 102.

Obviously, the shape of the surface is, in and of itself, of much criticality except to the extent it allows reasonably free access of the blood to the sacrificial joint 106. Curved, slotted, and other variations of the end surface are also contemplated in this invention.

Figure 3:
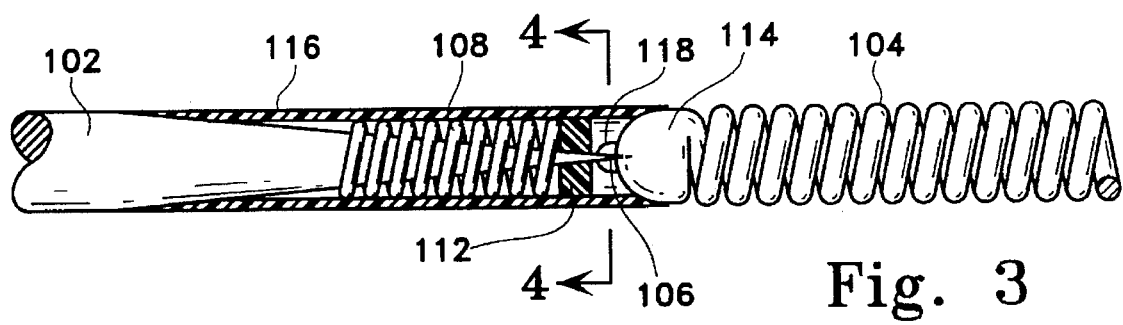
Figure 4:
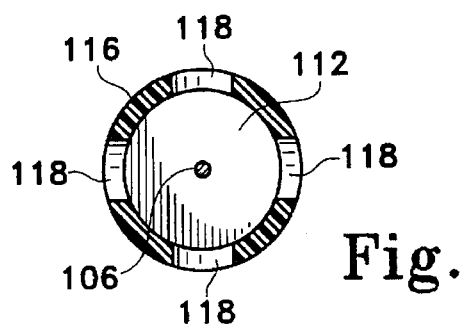
FIG. 4 shows a cross section of the variation shown in FIG. 3.

FIG. 3 shows a variation of the device shown in FIGS. 1 or 2 in that the core wire 102 comes down to a point having a sacrificial link 106 which is soldered into solder joint 114 in vasoocclusive device 104. The coil 108 provided to give additional column strength to the core wire 102 is also present. End plug 112 is also found in this device. The variation is in the outer sleeve 116. In this variation, the outer sleeve extends up to and is in contact with the solder joint 114 found at the end of vasoocclusive device 104. To allow the sacrificial link 106 to have electrical contact with the patient's blood, a sleeve 116 has a number of openings therein to allow contact of the blood with the sacrificial link 106. The openings 118 may be seen both in FIG. 3 and in a cross-section found in FIG. 4. The end plug 112 and the cross-section of the sacrificial link 106 may also be seen in FIG. 4. The variation shown in FIG. 3 may have slightly more physical strength but because of the smaller area through openings 118, the step of electrolysis may be slightly slower.

Figure 5:
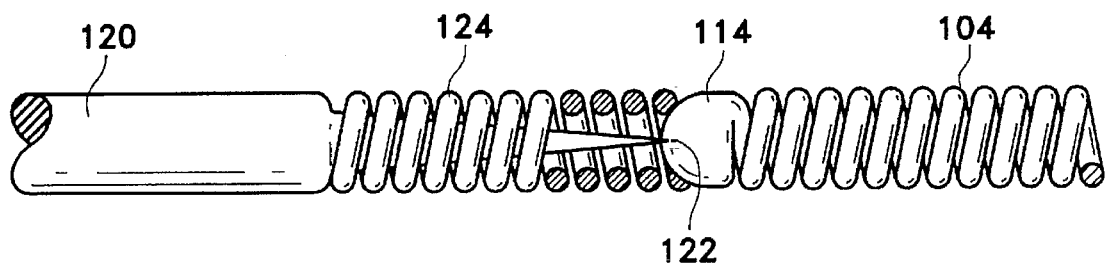

FIG. 5 shows another variation of the inventive sacrificial joint. The device again has a guidewire or core wire 120 which tapers down to a small point which is soldered into solder joint 114 on the end of vasoocclusive device 104. Again, as with the device in FIGS. 1, 2, and 3, all except the most distal portion 122 of core wire 120 is coated with an insulating material such as Teflon® polymer or other suitable insulating polymers. In this instance, however, the sacrificial link 122 forming the distal end of core wire 120 is surrounded, as is a portion of the taper on guidewire 120 with a release spring 124. Release spring 124 is attached to the guidewire body 120 but is not attached to the solder joint 114 on vasoocclusive device 104. The release spring 124 is slightly compressed. It, however, has some space between its adjacent windings as it is found in place on the core wire 120. In this way, blood has access to sacrificial link 122 between the adjacent windings on release spring 124. When the sacrificial link 122 is dissolved, release spring 124 gently pushes vasoocclusive device 104 away from the tip of the guidewire or core wire 120. Release spring 124 is completely insulated except, obviously, for the portion which is connected to the core wire 120, if welding or soldering of release spring 124 is had to core wire 120.

Figure 6:
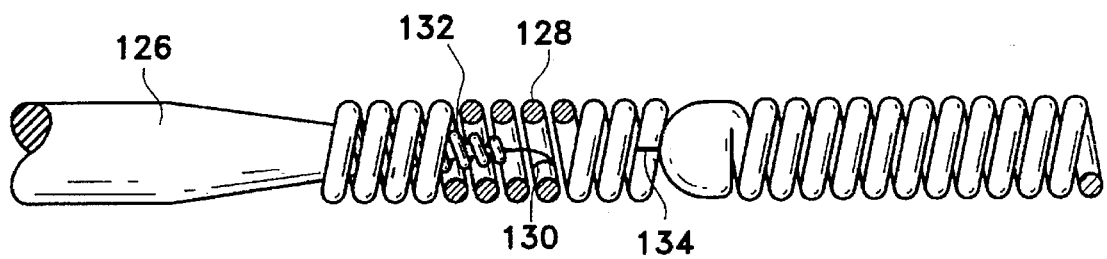
Figure 7:
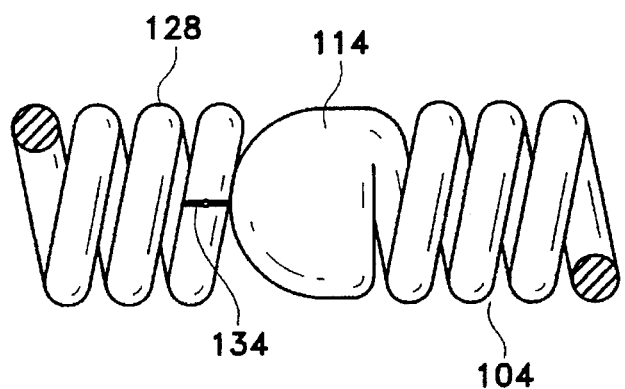
FIG. 7 shows a close up side view of a variation such as found in FIG. 6.

FIG. 6 shows a variation of the inventive device in which core wire 126 tapers down and is either directly soldered to the interior of coil 128 at solder joint 130 or is connected to a link which is then soldered at joint 130. A support spring 132 interior to coil 128 may be used in the same way as was shown in FIGS. 1, 2, and 3. As a safety factor, coil 128 and support spring 132 are fixed to core wire 126. The coil 128 is also electrically connected to core wire 126. All of core wire 126, coil 128, and support spring 132 are insulated so as to prevent electrolysis upon application of voltage to core wire 126. The exception to this insulation is a scribe or score mark 134 which forms the discrete sacrificial link. Score mark 134 is shown in more detail on FIG. 7. Again, the effect of the scribe or score mark 134 as shown in FIG. 6 is that the electrolysis takes place only at that small area and when the electrolysis has completely severed coil 128 at that point, there is little potential for electrolysis to take place at any other site on the core wire 126 or spring 128.

Vasoocclusive device 104 is shown in each of the drawings above to be a coil. It may be a coil or a braid or other vasoocclusive device as is already known. The vasoocclusive device may be covered or connected with fibrous materials tied to the outside of the coil or braided onto the outer cover of the coil as desired. Such fibrous adjuvants may be found in U.S. Pat. Nos. 5,382,259, to Phelps et al, or in 5,226,911, entitled "Vasoocclusion Coil with Attached Fibrous Elements", the entirety of which are incorporated by reference.

In addition to the use of shrink-wrap tubing containing polyethylene, polypropylene, polyurethane, polyethylene terephthalate, polyvinylchloride, or the like as insulator on the core wire, another desirable thermoplastic is generically known as parylene. There are a variety of polymers (e.g., polyxyxylene) based on para-xylylene. These polymers are typically placed onto a substrate by vapor phase polymerization of the monomer. Parylene N coatings are produced by vaporization of a di(P-xylylene) dimer, pyrollization, and condensation of the vapor to produce a polymer that is maintained at a comparatively lower temperature. In addition to parylene-N, parylene-C is derived from di(monochloro-P-xylylene) and parylene-D is derived from di(dichloro-P-xylylene). There are a variety of known ways to apply parylene to substrates. Their use in surgical devices has been shown, for instance, in U.S. Pat. Nos. 5,380,320 (to J. R. Morris), in 5,174,295 (to Christian et al.), in 5,067,491 (to Taylor et al.) and the like. Since the inventive device is a one-use device, various of the parylenes are suitable, particularly in the area of the electrolytically severable joint as an external insulating layer. This is especially true when the coated device is annealed.

One highly desirable variation of this invention is one in which at least the region near the electrolytically severable joint is coated with parylene and a very narrow band is removed using, e.g., a laser to form the sacrificial joint. Coatings of less than about 0.001" is highly desirable, preferably less than about 0.00075".

Figure 8:
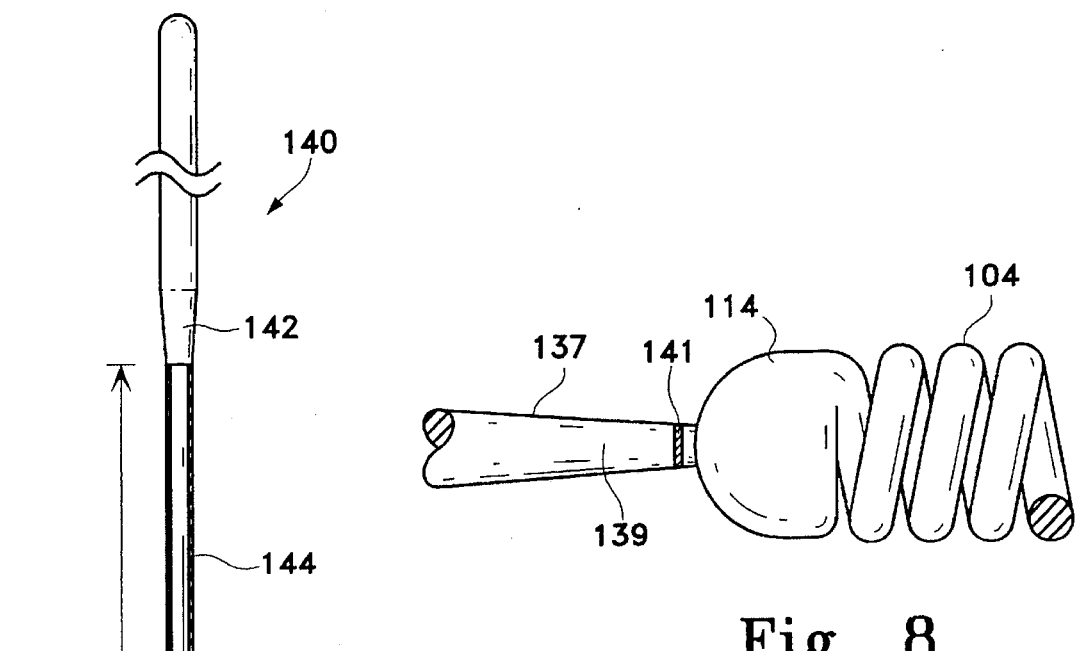
FIG. 8 shows side view of an assembly involving the laser-scribed sacrificial link of this invention.

Specifically, in FIG. 8, a joint similar to that shown in FIG. 5 or 6 is deployed. The device has a guide wire or core wire 137 which tapers down to a small point which is incorporated into solder joint 114 on the end of vasoocclusive device 104. At least the portion of the core wire 137, visible in FIG. 8, is coated with parylene coating 139. The core wire 137 distal of the view seen in FIG. 8 may also be coated with parylene as needed or desired. A laser-scribed region 141 is prepared by cutting away the previously coated parylene by use of a laser. An ultraviolet excimer laser of appropriate power is suitable. The width of the laser-scribed region 141 is quite narrow, typically no more than about 0.010 inches preferably no more than about 0.005 inches. The laser-scribed region 141 may be adjacent the solder joint 114 or weld joint; this will result in a clean "tail" to the coil after it its deployed. The laser-scribed region 141 may be any place in that region, however.

This procedure has proven to be reliable and consistently produces good joints with predictable deployment times.

We have also found that the use of a polyfluorocarbon spray, e.g., PTFE solids in a suitable solvent carrier, is also useful in producing an insulator layer for the core wire portion of the assembly, particularly the portion of the core wire proximal of the sacrificial joint.

Said another way, at least a portion of the region of the assembly distal of the sacrificial joint is covered with a polymeric coating selected from one or more of the polymers listed above; the region usually need not extend to the bushing or coil solder joint mentioned elsewhere. The region of the core wire assembly proximal of the sacrificial joint may also be covered with a polymeric coating selected from one or more of the polymers listed above; the insulated region usually need not extend very far into the catheter but may do so.

Figure 9:
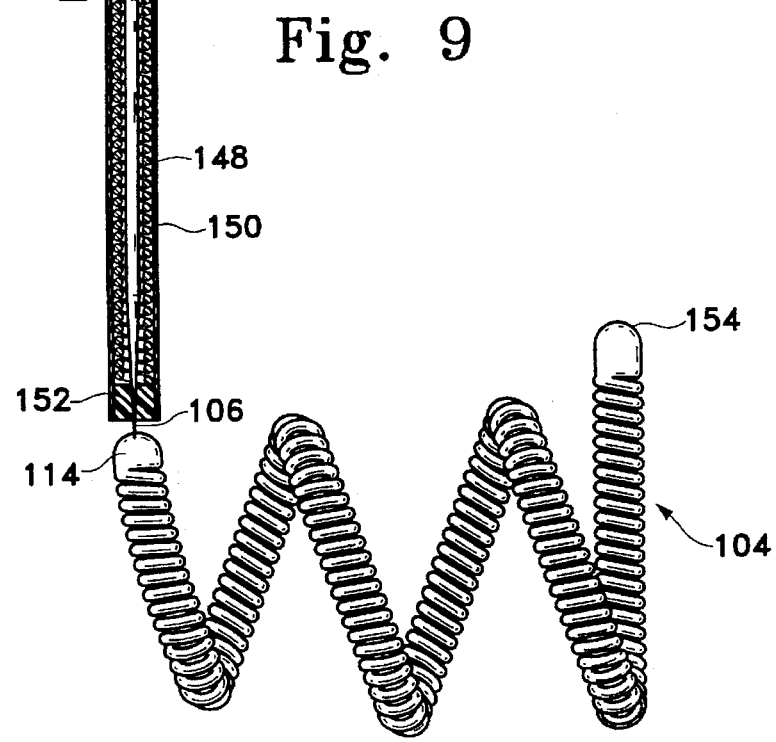
FIG. 9 shows side view of a typical assembly involving the sacrificial link used in this invention.

FIG. 9 shows a typical layout involving the inventive discrete sacrificial joint 106 as was generally shown in the Figures above. In FIG. 9, a somewhat conventional Teflon® laminated or similarly insulated stainless steel guidewire assembly 140 may be placed within a protective catheter. As was noted above, stainless steel guidewire 140 may have a diameter of approximately 10–30 mils. In the noted embodiment in FIG. 9, guidewire assembly 140 is tapered at its distal end to form a conical section 142 which joins a further section 144 which extends along a length of guidewire 146. Section 144 then gradually narrows down to a thinner section 148. The guidewire assembly 140, as noted above, may be placed within a catheter body and is typically 50–200 cm. in length down to sacrificial link 106. As was shown in FIG. 1, the distal section of guidewire assembly 140 has an outer Teflon® sleeve 150 (or sleeve of other appropriate insulating material). Furthermore, it has an end plug 152 to permit isolation of the guidewire electrically from the blood except at sacrificial discrete link 106. The proximal end of vasoocclusive device 104 is typically a soldered tip or a joint 114. Preferably, vasoocclusive device 104, when a coil, forms a secondary loop after it emanates from the end of the catheter. The distal end of vasoocclusive device 104 may also have an end plug or tip to prevent punctures of the aneurysm when introduced into the aneurysm sac.

As noted, the coil or vasoocclusive device 104 may be pre-biased to form a cylinder or conical envelope. However, the vasoocclusive device 104 is extremely soft and its overall shape is easily deformed. When inserted within the catheter (not shown), the vasoocclusive device 104 is easily straightened so to lie axially within the catheter. Once ejected from the tip of the catheter, vasoocclusive device 104 may form a shape shown in FIG. 9 or may be loosely deformed to conform to the interior shape of the aneurysm.

Figure 10:
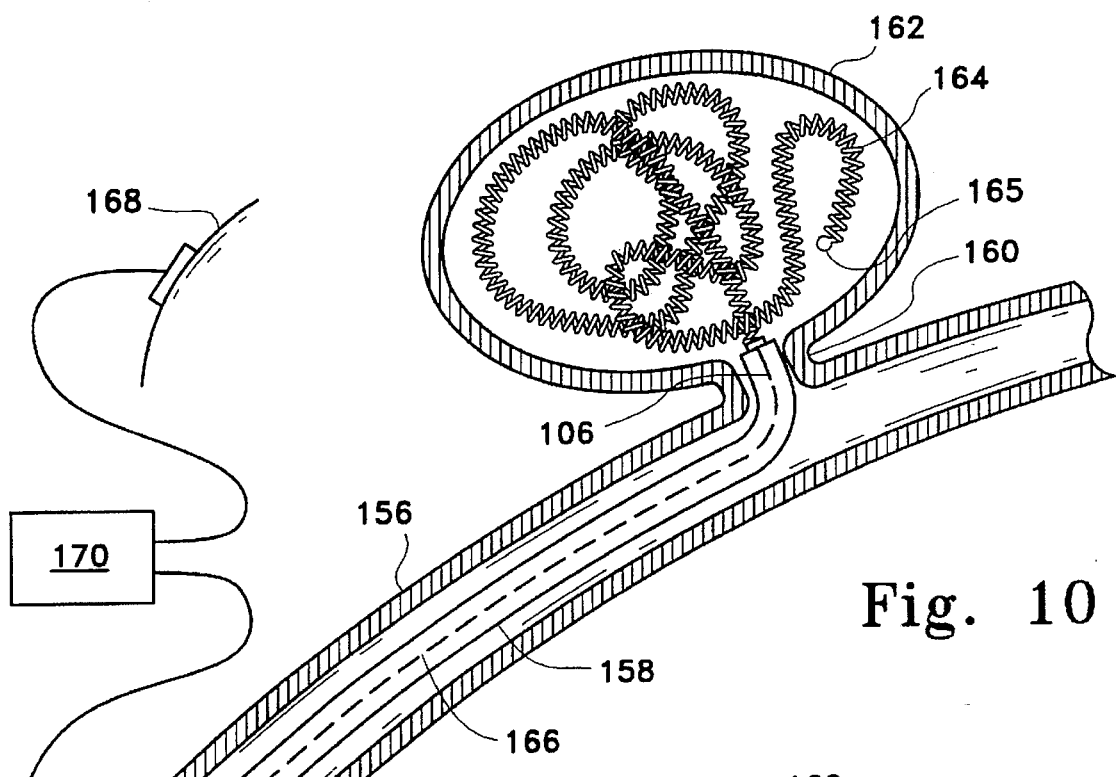
FIGS. 10 and 11 schematically depict the method for deploying the vasoocclusive device using the inventive sacrificial link.

FIG. 10 shows the placement of the inventive devices shown above within a vessel 156 with the tip of catheter 158 placed near neck 160 of aneurysm 162. Vasoocclusive device 164 is fed into aneurysm 162 at least until sacrificial link 106 is exposed beyond the distal tip of the catheter 158. A positive electric current of approximately 0.01–2 milliamps at 0.1–6 volts is applied to guidewire 166 to form a thrombus within aneurysm 162. The negative pole 168 of power supply 170 is typically placed in electrical contact with the skin.

After the thrombus has been formed and the aneurysm occluded, vasoocclusive device 164 is detached from guidewire 166 by electrolytic disintegration of sacrificial link 106.

Figure 11:
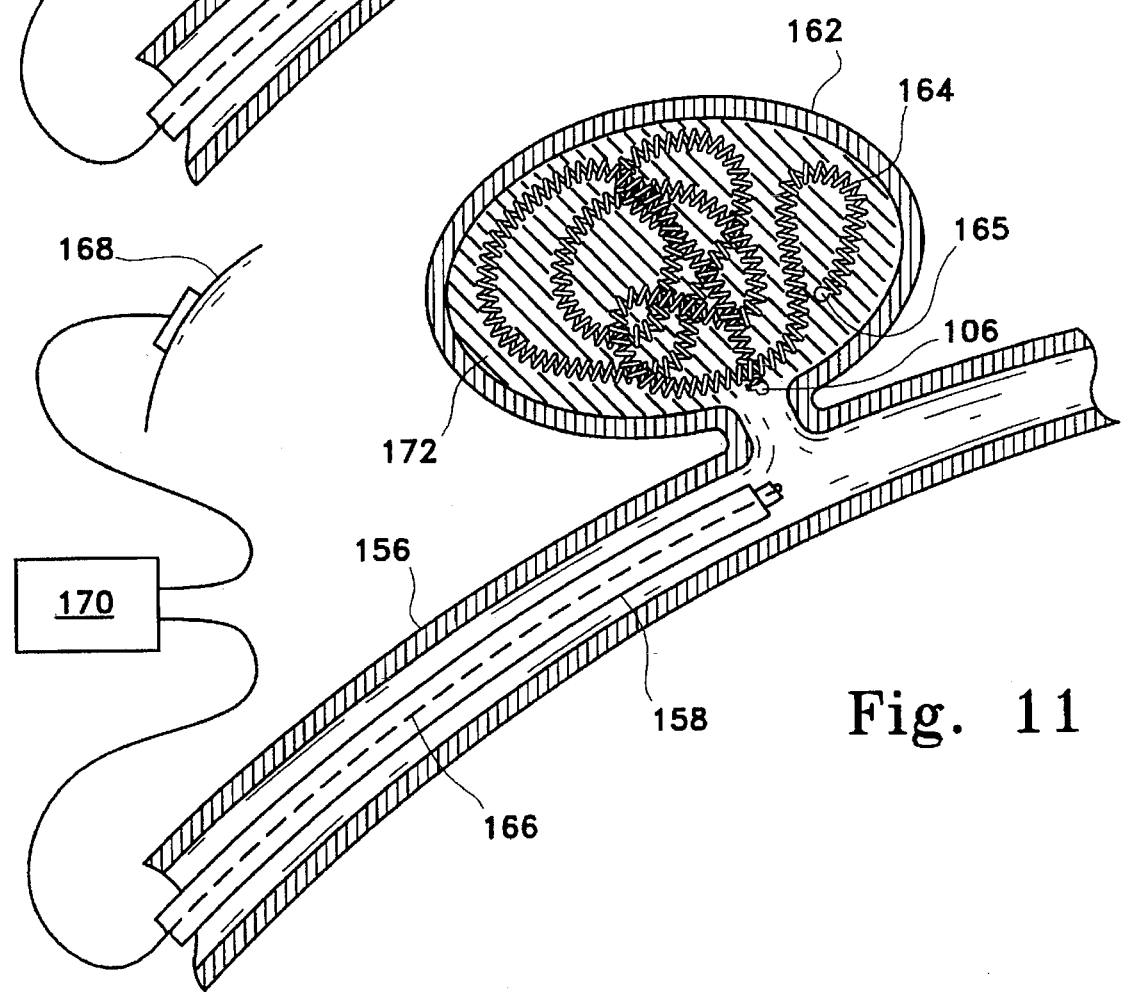

After sacrificial link 106 is at least mostly dissolved by electrolytic action, typically in less than two minutes, most often in less than one minute, the guidewire 166, catheter 156, are removed vessel 156, leaving aneurysm 162 occluded as shown in FIG. 11.

The process is typically practiced under fluoroscopic control with local anesthesia. A transfemoral catheter is utilized to treat a cerebral aneurysm and is usually introduced at the groin. When the vasoocclusive device 164 is platinum, it is not effected by electrolysis. When the guidewire and pertinent portions of the supporting coils at the distal tip of the guidewire are adequately coated with insulating coverings, only the exposed portion at the sacrificial link 106 is effected by the electrolysis.

Many alterations and modifications may be made by those having ordinary skill in the art without departing from the spirit and scope of the invention. Therefore, it must be understood that the shape of the tip or distal platinum coil used in combination with the guidewire according to the invention may be provided with a variety of shapes and envelopes.

The illustrated embodiments have been used only for the purposes of clarity and should not be taken as limiting the invention as defined by the following claims.

We claim as our invention:

1. A guidewire for use in the formation of a vascular occlusion, in combination with a catheter, comprising:

a core wire, said core wire having an axis and not being susceptible to electrolytic disintegration in blood, a discrete, sacrificial, severable link having a diameter and which is susceptible to electrolytic disintegration in blood distal to and severably connected to said core wire, wherein said link has a length no greater than the diameter of the link or that the surface of the link after disintegration is not substantially greater than would be a circle having the diameter of the link, and wherein said core wire is insulated proximally of the link with at least one layer of an adherent polymeric covering and an elongate tip portion extending distally beyond said core wire and adapted to form said occlusion at a selected site within a mammal vasculature, said elongate tip portion not being susceptible to the electrolytic disintegration in blood, insulated just distally of the link with at least one layer of an adherent polymeric covering, and said elongate tip is severable from the core wire upon an electrolytic disintegration of the sacrificial link.

2. The guidewire of claim 1 wherein said adherent polymeric coverings are of materials selected from the group consisting of polyfluorocarbons, polyxyxylene, polyethylene, polypropylene, polyurethane, polyimides, and silicone polymers.

3. The guidewire of claim 2 wherein at least one of the adherent polymeric coatings is a polyfluorocarbon.

4. The guidewire of claim 3 wherein at least one of the adherent polymeric coatings is a polytetrafluoroethylene.

5. The guidewire of claim 2 wherein at least one of the polymeric coatings is a polyxyxylene.

6. The guidewire of claim 2 wherein the discrete sacrificial link is a is a groove produced by laser scoring through a polymeric coating.

7. The guidewire of claim 1 wherein the elongate tip section is a coil.

8. The guidewire of claim 7 wherein the elongate tip section comprises a platinum alloy coil.

9. The guidewire of claim 1 wherein the core wire is electrically connected to a coil located coaxially about the axis of the core wire and which is electrically insulated from surrounding blood.

10. The guidewire of claim 9 wherein the discrete sacrificial link is a score in the insulation on the coaxial coil.

* * * * *

UNITED STATES PATENT AND TRADEMARK OFFICE
CERTIFICATE OF CORRECTION

PATENT NO. : 5,624,449
DATED : April 29, 1997
INVENTOR(S) : Pete P. Pham, et al.

It is certified that error appears in the above-identified patent and that said Letters Patent is hereby corrected as shown below:

At column 2, line 51, insert -- of -- after the word variety.

At column 6, line 57, delete "its" and substitute therefor -- is --.

At column 8, line 54, delete the first occurrence of "is a".

Signed and Sealed this

Twenty-fourth Day of March, 1998

Attest:

BRUCE LEHMAN

Attesting Officer

Commissioner of Patents and Trademarks